(12) United States Patent
Staal

(10) Patent No.: US 6,258,435 B1
(45) Date of Patent: Jul. 10, 2001

(54) HYGIENE MATS

(76) Inventor: Johan Staal, Hammerweg 39, 7731 AH Ommen (NL)

( * ) Notice: Subject to any disclaimer, the term of this patent is extended or adjusted under 35 U.S.C. 154(b) by 0 days.

(21) Appl. No.: 09/195,450

(22) Filed: Nov. 18, 1998

(30) Foreign Application Priority Data

Nov. 18, 1997 (NL) .................................................. 1007566

(51) Int. Cl.⁷ ...................................................... B32B 5/18
(52) U.S. Cl. ........................... 428/71; 15/104.93; 15/215; 15/217; 428/76; 442/221; 442/287
(58) Field of Search .................................... 442/221, 287; 428/71, 76, 95, 319.9; 15/104.92, 104.93, 215, 216, 217

(56) References Cited

U.S. PATENT DOCUMENTS

| | | |
|---|---|---|
| 2,989,965 | 6/1961 | Rod . |
| 3,083,393 | 4/1963 | Nappi . |
| 5,164,164 | 11/1992 | Strickler et al. . |
| 5,792,712 | * 8/1998 | Hori et al. ............................ 442/123 |
| 6,027,777 | * 2/2000 | Hirano et al. ........................ 428/35.4 |

FOREIGN PATENT DOCUMENTS

| | | |
|---|---|---|
| 84 563 | 5/1895 | (DE) . |
| 26 39 289 | 3/1978 | (DE) . |
| 0 060 148 | 9/1982 | (EP) . |
| 2 761 255 | 10/1998 | (FR) . |
| 2 268 399 | 1/1994 | (GB) . |
| 69 03 225 | 12/1969 | (NL) . |

* cited by examiner

Primary Examiner—Blaine Copenheaver
Assistant Examiner—Ula C. Ruddock
(74) Attorney, Agent, or Firm—Young & Thompson

(57) ABSTRACT

A disinfecting mat includes a spongy core retaining a liquid disinfectant and a cover completely enclosing the core, where the cover has a top surface with an annular top edge and a top central mat portion that is liquid permeable. The core is contained in a water impermeable frame with a bottom and sides that contain the cover and with an inwardly extending annular lip that extends over at least a part of the annular top edge while leaving the top central mat portion open. The liquid permeable top central mat portion allows the disinfectant to puddle in areas of the top central mat portion that are depressed during use.

7 Claims, 7 Drawing Sheets

HYGIENE MATS

BACKGROUND OF THE INVENTUON

Figure 1:
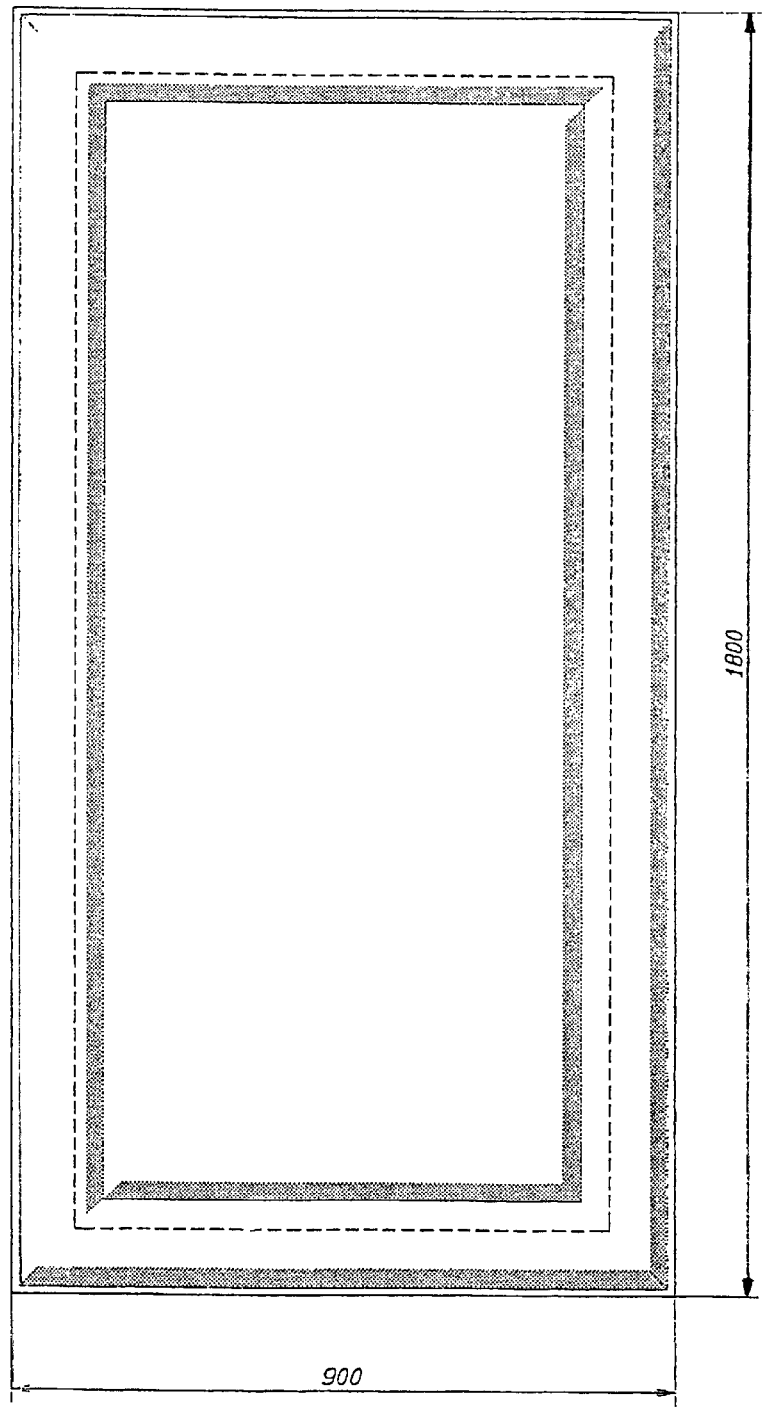
Figure 1:
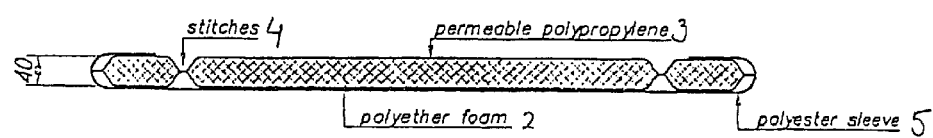

The present invention relates to hygiene mats on which users, e.g. visitors, can disinfect the soles of their shoes or boots, before they enter into a bamn or the like.

At many farms it is common practice to try to exclude contamination through shoes and/or boots by placing open containers with disinfection fluids at the entrances. Visitors can disinfect their shoes and boorts by 'dipping' their feet into the container filled with disinfection liquid. Many of these continers arm cut out plastic jerrycans which contain variable quantities of liquid that pollute quickly and in which visitors are unable to disinfect their shoes or boots without running the risk of getting wet feet.

SUMMARY OF THE INVENTION

The invention relates to a combination of a liquid retaining mat, which is substantially fully surrounded by a wear resistant, permeable fabric material, fitted in a waterproof sleeve to prevent leaking of the liquid into the environment.

In particular, the hygiene mats according to the present invention comprise an absorbing mat which is covered on substantially all sides by a protective, woven, permeable polypropylene material and supplied with a waterproof sleeve which is open on the top side in order to contain disinfecting liquid(s).

The mats can be manufactured in different sizes for different applications to replace the known open 'footbaths', pieces of carpet or foam rubber.

Based on the above principle, the present invention aims to provide for more than one application.

The invention aims to be a quality medium to disinfect the shoes or boots of visitors to the premises, or alternatively the equipment, like the wheels of farm transport means. carts, forklifttrucks and furthermore the wheels of cars and lonies. In this connection, the invention aims to provide a reservoir for disinfecting liquid, without hard, upstanding edges, where an easy application and passage is combined with a longer contact between the object to disinfect and the disinfecting liquid. In the case of persons using the hygiene mats, said longer contact is caused by the fact that a user can stand on the mat with both feet, without liquid running over and into bis shoes. In case the mats are being used by transport means, it is prevented that said means have to pass over elevations or edges in or on the floor.

The invention also aims to be an alternative to the partial care of the feet or claws of farm animals like cattle and sheep In this case the mat is provided with a caring or disinfecting, or another purpose serving, product. The animals are made to walk over the mat and consequently come into contact with the product contained in the mat.

The latter purpose of the invention is advantageous as animals have a natural dislike for open surfaces of water and tend to jump over such surfaces or containers providing such surfaces. Furthermore they have the reflex to manure in the resrvoir or water surface when they are forced to pass it.

BRIEF DESCRIPTION OF THE PREFERRED EMBODIMENTS

The above and other objects and advantages of the present invention will become apparent from the following description when read in conjunction with the accompanying drawings, wherein:

FIG. 1 shows schemhatically a top view of the hygiene mat according to the present invention in a first embodiment; and FIG. 2 –FIG. 7 show hygiene mats according to further embodiments.

DETAILED DESCRIPTION OF THE PREFERRED EMBODIMENTS

As mentioned in the above, the mats according to the invention may be used for different applications, namely as:

1. disinfecting mat for persons;
2. disinfecting mat for equipment; and
3. claw mat for animals Depending on the application, the measurements of the mats will vary. The construction principle of the mat according to the invention is as follows. The mat 1 comprises a liquid retaining core, in particular a polyether core, indicated by reference numeral 2, which is surrounded by a permeable material layer 3 that prevents polution and wear of the core and therefore increases the life thereof. Preferably, the permeable material layer 3 is made of polypropylene.

The polyether core, or polyether foam, 2 advantageously comprises polyether SG 20 to SG 40, and preferably has a thickness of 20 mm –80 mm. The permeable protection of polypropylene preferably has a density of 265 $g/m^2$ and comprises quality 24119 from Nicolon TenCate®.

In order to improve the strength of the construction, the mat is preferably stitched at about 10–15 cm from the edges thereof. Said stitches are indicated with reference numeral 4.

The core 2, surrounded with the material layer 3, is provided with a cover 5 which is meant to function as a container restraint for a liquid to be contained in the core. Preferably, the cover 5 comprises a double coated polyester material. Preferably, the density of the polyester material is 650 $g/m^2$.

As shown in the drawings, the cover 5 covers the bottom and the sides of the core, and covers only partially the top thereof. A person using the mat will step on said mat in the non-covered area and will come into contact with the liquid retained in the core thereof. As mentioned in the above, the liquid may be a disinfecting liquid or any other liquid, such as a caring liquid.

Because of the close surrounding of the cover 5 on the core 2 with the material layer 3, the disinfecting liquid is pushed upwards whenever the mat is being stepped on. The location where a person puts his feet down on the mat will be compressed and liquid will flow immediately to this lowest point and will surround the shoes of boots of said person. In the case of an animals, the claws of said animal will be surrounded by the liquid and in the case of transport equipment, the wheels thereof will be surrounded.

Figure 2:
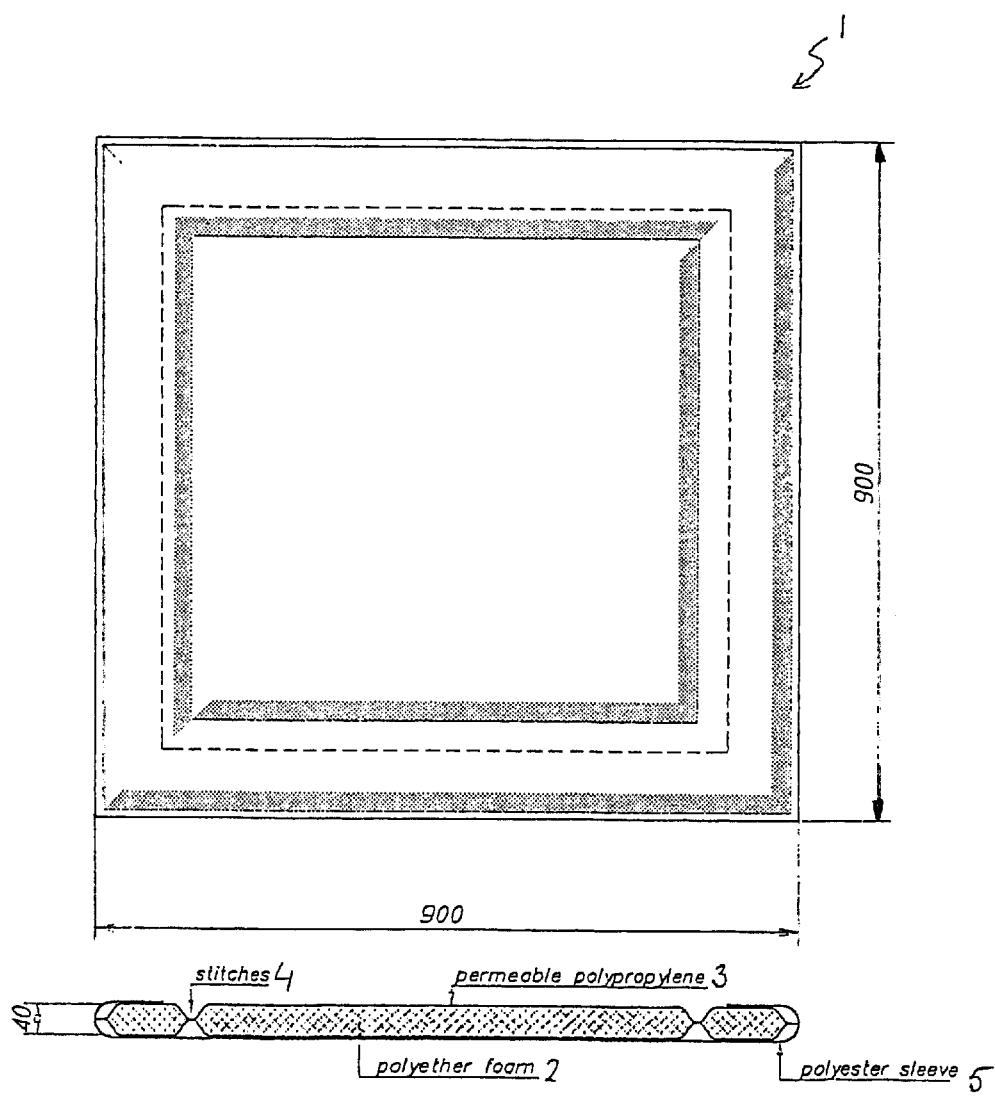
Figure 3:
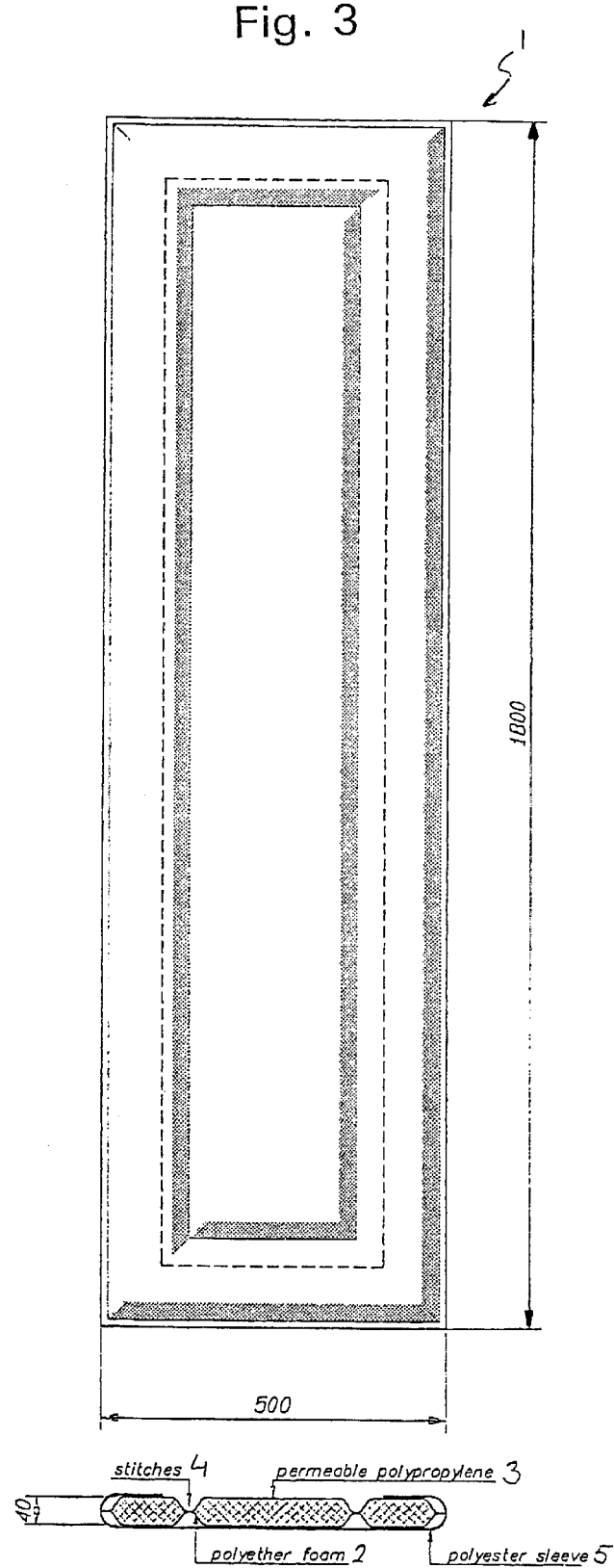
Figure 4:
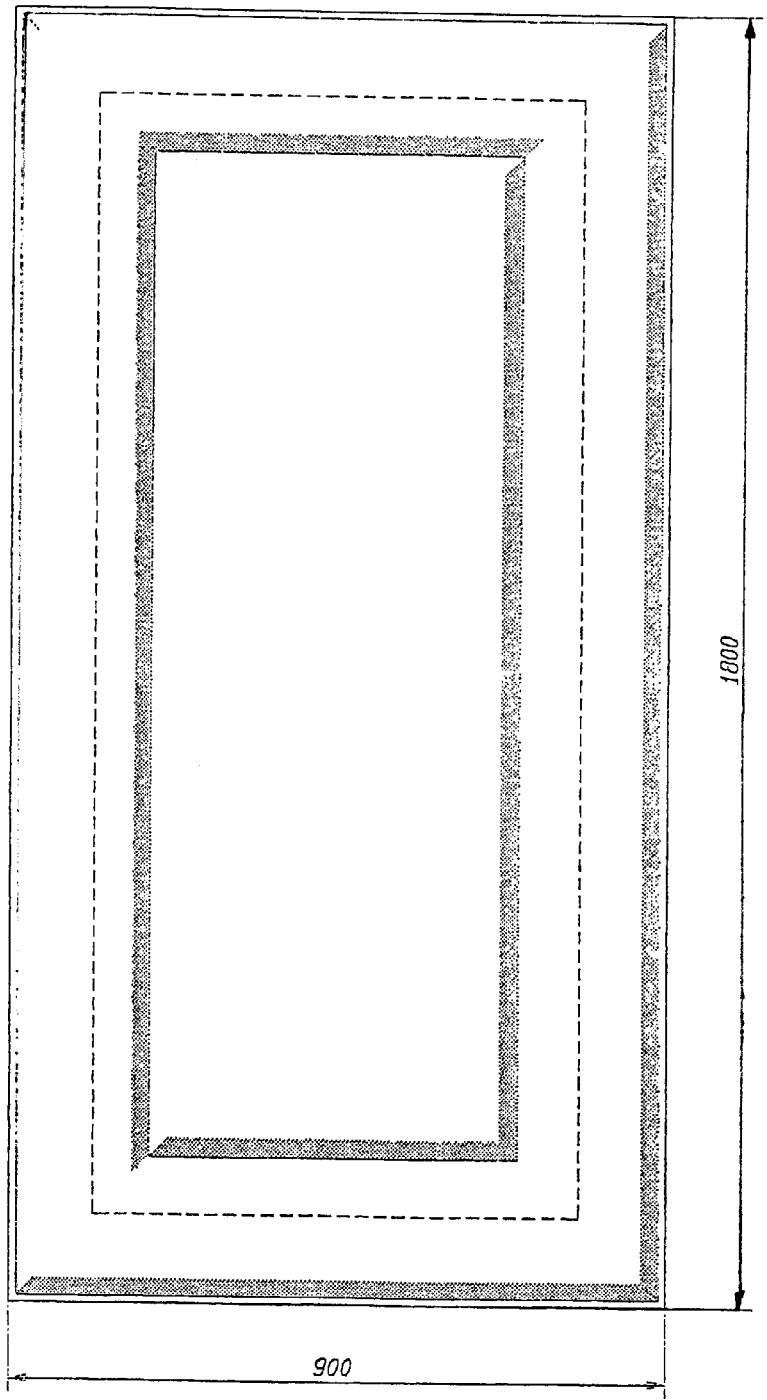
Figure 4:
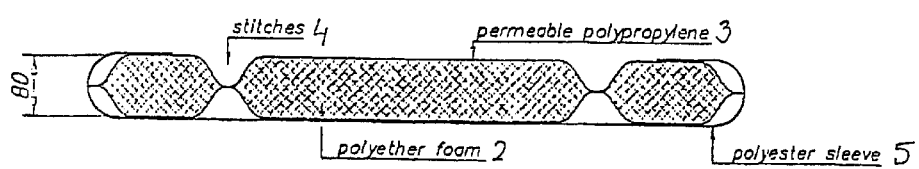
Figure 5:
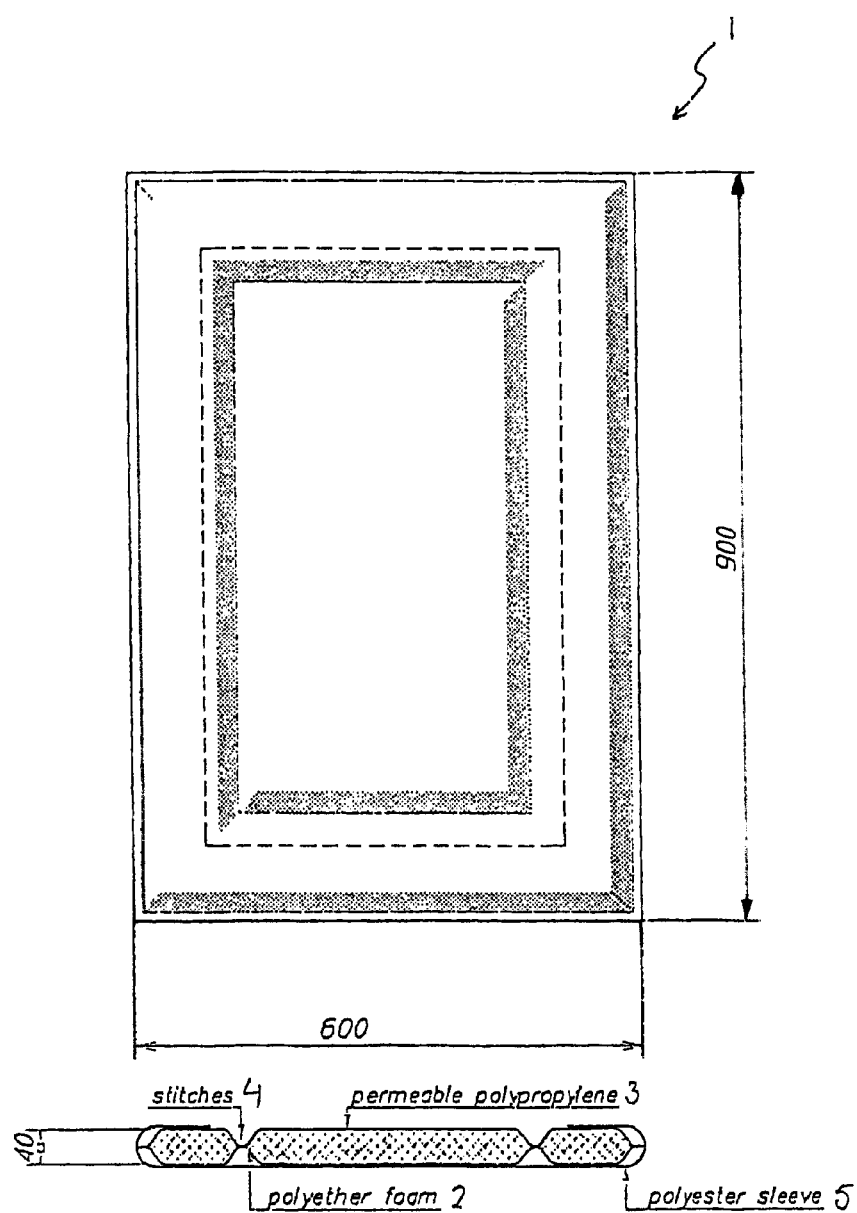
Figure 6:
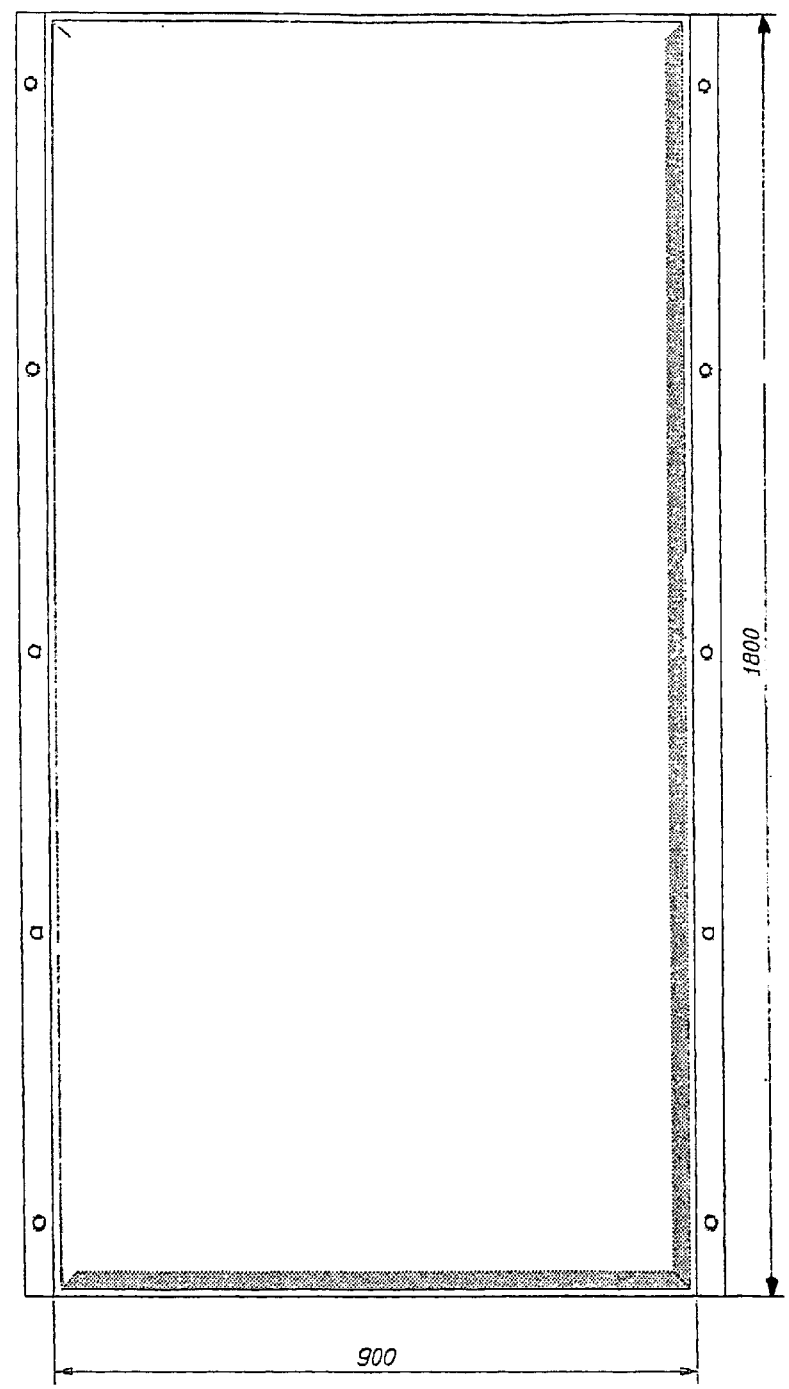
Figure 6:
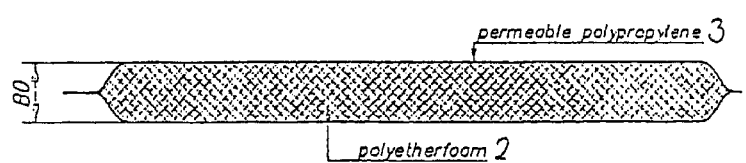
Figure 7:
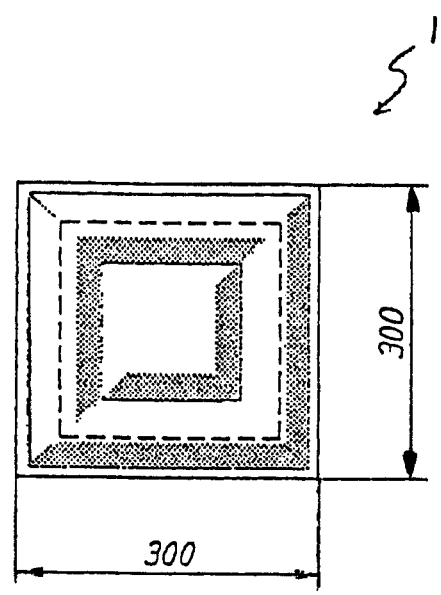
Figure 7:
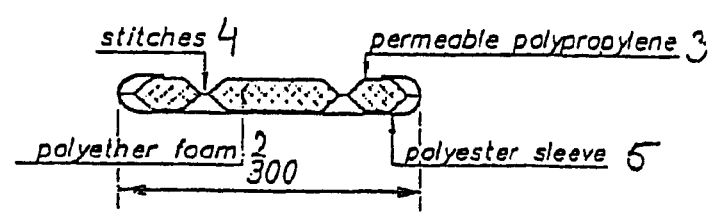

The measurements of the mats according to FIGS. 1–7 vary and are as follows:

FIG. 1 1800×900×40 mm (l×w×h)
FIG. 2 900×900×40 mm (l×w×h)
FIG. 3 1800×500×40 mm (l×w×h)
FIG. 4 1800×900×80 mm(l×w×h)
FIG. 5 900×600×40 mm(l×w×h)
FIG. 6 1800×900×80 mm(l×w×h)
FIG. 7 300×300×32 mm (l×w×h)

What is claimed is:

1. A mat comprising a liquid retaining core, surrounded by a permeable material, and fitted in a waterproof sleeve, said sleeve covering the bottom, the sides and only partially covering the top of said core, said sleeve containing a liquid, wherein when said mat is depressed leakage of said liquid into the environment is prevented, exposing a portion of the permeable material.

2. Mat according to claim 1, wherein the core comprises a polyether core.

3. Mat according to claim 2, wherein the permeable material comprises polypropylene.

4. Mat according to claim 2, wherein the waterproof sleeve comprises polyester.

5. Mat according to claim, wherein the permeable material comprises polypropylene.

6. Mat according to claim 5, wherein the waterproof sleeve comprises polyester.

7. Mat according to claim 1, wherein the waterproof sleeve comprises polyester.

* * * * *